United States Patent
Scammell

(10) Patent No.: US 6,248,366 B1
(45) Date of Patent: Jun. 19, 2001

(54) LIQUID COLOSTRUM FOR DAIRY PRODUCTS

(75) Inventor: Antony William Scammell, College Park (AU)

(73) Assignee: Northfield Laboratories Pty Ltd. (AU)

( * ) Notice: Subject to any disclaimer, the term of this patent is extended or adjusted under 35 U.S.C. 154(b) by 0 days.

(21) Appl. No.: 09/567,401

(22) Filed: May 9, 2000

Related U.S. Application Data

(62) Division of application No. 09/068,358, filed as application No. PCT/AU96/00708 on Nov. 8, 1996.

(30) Foreign Application Priority Data

Nov. 8, 1995 (AU) .................................................. PN 6427

(51) Int. Cl.⁷ .............................. A01J 11/00; A23C 3/00
(52) U.S. Cl. ...................... 424/535; 424/157.1; 99/452; 99/496
(58) Field of Search ................................ 424/535, 157.1; 99/452, 496; 436/22

(56) References Cited

U.S. PATENT DOCUMENTS

| | | | |
|---|---|---|---|
| 3,058,833 | 10/1962 | Simonart | 99/212 |
| 4,342,747 | 8/1982 | Liotet et al. | 424/95 |
| 5,143,727 | 9/1992 | Ebina | 424/89 |

FOREIGN PATENT DOCUMENTS

| | | |
|---|---|---|
| 6467465 | 4/1967 | (AU) . |
| 3934089 | 2/1990 | (AU) . |
| 6313694 | 12/1995 | (AU) . |
| 668033 | 4/1996 | (AU) . |
| 9308264 | 4/1993 | (WO) . |
| 9310818 | 6/1993 | (WO) . |
| 9416675 | 8/1994 | (WO) . |
| 9510192 | 4/1995 | (WO) . |

OTHER PUBLICATIONS

Eckles, Clarence Henry, et al. "Common Dairy Processes." Milk and Milk Products, Fourth Edition, (1951) pp. 183–187.

Julicher, Von B., et al., "Uber den Effekt einer Entkeimungszentrifuge auf den Gehalt an Lipopolysacchariden und Sporen in Milch", vol. 44, No. 9 (1989), pp. 564–568.

*Primary Examiner*—Laurie Scheiner
(74) *Attorney, Agent, or Firm*—Ladas and Parry

(57) ABSTRACT

The present invention relates to dairy compositions and, more particularly, to dairy compositions containing colostrum. The applicant has discovered that colostrum can be processed so as to reduce the bioburden of liquid colostrum while retaining the biological activity of certain proteins including the immunoglobulin fraction. By this process it is possible to introduce liquid colostrum into pasteurized and unpasteurized dairy products. In one aspect of the invention there is provided a process for the preparation of a liquid colostrum product, suitable for inclusion in dairy products, which process includes subjecting colostrum to centrifugation to substantially reduce the microbial content thereof.

8 Claims, No Drawings

LIQUID COLOSTRUM FOR DAIRY PRODUCTS

This application is a Divisional of application Ser. No. 09/068,358, filed May 7, 1998 which is a 371 of PCT/AU96/00708 Nov. 8, 1996.

The present invention relates to dairy compositions and, more particularly, to dairy compositions containing colostrum.

Raw milk contains between 0% and 1.0% immunoglobulin. However, for safety reasons milk for human consumption is pasteurised—typically at 72° C. for 15 seconds or 132° C. for at least one second (UHT). Each of these heat treatments is sufficient to denature the immunoglobulin found in raw milk and also to denature certain other milk proteins such as, for example, certain growth factors.

The maximum cfu/mL allowed in milk (Australian Food Standard H1) that has been pasteurised according to the accepted methods is 50,000 cfu/mL. In practice the counts in pasteurised milk at time of manufacture are usually less than 10,000 cfu/mL.

Colostrum is the secretion obtained from female mammals just before and for a short period after giving birth. Raw colostrum contains up to 10% immunoglobulin as well as other proteins such as growth factors. However, colostrum is routinely excluded from milk processing due to its very different composition which negatively affects processing efficiency and dairy product quality. Raw colostrum cannot be added to milk products for human consumption due to its bioburden. Colostrum cannot be pasteurised by standard methods without denaturing biologically active proteins such as antibodies. When subjected to heat treatment of greater than approximately 65° C., colostrum will typically undergo sever chemical change leading to the failing of dairy processing equipment.

It is an object of the present invention to overcome, or at least alleviate, one or more of the difficulties or deficiencies associated with the prior art.

The applicant has discovered that colostrum can be processed so as to reduce the bioburden of liquid colostrum while retaining the biological activity of certain proteins including the immunoglobulin fraction. By this process it is possible to introduce liquid colostrum into pasteurised and unpasteurised dairy products including, for example, milk, skim milk, flavoured milks, other modified milks, yoghurts (natural, flavoured, drinking, frozen), other probiotic formulations, cheese formulations such as cheese sticks, and ice creams.

Accordingly in a first aspect of the present invention there is provided a process for the preparation of a liquid colostrum product, suitable for inclusion in dairy products, which process includes subjecting colostrum to centrifugation to substantially reduce the microbial content thereof.

The colostrum may be freshly harvested colostrum or frozen colostrum. The colostrum may be bovine, ovine or caprine colostrum harvested from freshly calved animals. The colostrum may be harvested using modern milking equipment. Preferably the colostrum is from one or more of the approximately first to tenth milkings after calving. The colostrum may be antibody enriched. For example the colostrum may be from a mammal hyperimmunised against specific pathogens of relevance to human or other diseases.

Specific pathogens which may be used to hyperimmunise the mammal include one or more of:

1) *Cryptosporidium enteridies, Cryptosporidium parvum,*
2) *Isoporo belli,*
3) *Giardia sp,*
4) Cytomegalovirus sp,
5) *Salmonella sp,*
6) *Shigella sp,*
7) *Candida sp,*
8) Rotavirus,
9) *Blastocystis hominis,*
10) *Herpes simplex* virus,
11) Entero-toxigenic *E. Coli,*
12) *Aeromonas sp,*
13) *Mycobacterium Avium* intracellular,
14) *Yersinia entero colitica,*
15) *Toxoplasma gondii,*
16) Clostridium sp.,
17) *Campylobacter jejuni/coli,*
18) *Entamoeba histolytica,*
19) Human immunodeficiency virus
20) *Helicobactor pylori,*
21) Cholera sp.,
22) Respiratory syncitial virus
23) *Heamophilus influenzea*
24) Astrovirus
25) Adenovirus
26) Mycobacterium spp.
27) Calici virus
28) Toro virus The colostrum may be from a mammal hyperimmunised against specific proteins or enzymes such that the specific antibodies produced are of relevance in the prevention or treatment of human diseases or metabolic disorders.

The bacteria-removing centrifugation may be performed at a speed of approximately 7000–8000 rpm, preferably approximately 7400 rpm, to generate approximately 11,000 g to 14,000 g at approximately 1100 L per hour, preferably 12,000 g at approximately 1100 L per hour. An Alfa Laval Bactofuge has been found to be suitable.

Ideally, it is preferable that the centrifugation is performed by controlling throughput and thereby residence time of the colostrum such that the microbial content is reduced to less than 500 organisms per ml, preferably 200 organisms per ml, most preferably less than 50 organisms per ml.

Preferably, the centrifugation is conducted at a temperature of approximately 50° C. to approximately 64° C. More preferably, the centrifugation is conducted at a temperature of approximately 55° C. to approximately 63° C.

Following centrifugation, the colostrum may be chilled to below approximately 10° C., preferably to below approximately 4° C.

In a preferred form, the process of this aspect of the invention may include the preliminary step of separating the colostrum. Preferably the colostrum is separated into a light phase (cream) and a heavy phase (skim) Preferably the light phase is discarded and the heavy phase is processed according to the present invention.

Any suitable separation apparatus may be used. A preferred separation apparatus is a self desludging type apparatus.

Preferably the colostrum is pre-heated to a temperature of approximately 50° C. to approximately 64° C., more preferably approximately 55° C. to approximately 63° C., for a period of approximately 3–60 minutes, more preferably approximately 30 minutes, post the separation step. Any suitable means may be used to preheat the colostrum, for example a plate heat exchanger.

It will be understood that the steps of the process of this aspect of the present invention may take place in any suitable order. Other steps may also be included in the process of the present invention. For example in preferred embodiment of the process casein is removed from the colostrum by precipitation. Preferably this step takes place after the colostrum has first been subjected to a separation step and the light phase has been discarded, and then subjected to centrifugation according to the present invention.

In a further preferred embodiment of the process the colostrum is concentrated by means of ultrafiltration and/or evaporation and/or reverse osmosis. Preferably this step takes place after either the centrifugation or, if relevant, after the casein removal.

In a still further preferred embodiment of the process the colostrum is sterile filtered. Preferably this step takes place after the casein removal.

The method according to the present invention gives results that are consistently better than the results gained with standard pasteurisation and allows for the addition of colostrum to pasteurised dairy products and/or the processing of dairy products including a colostrum component with little or no diminution of the shelf life/stability expected with normal dairy products. For example, colostrum may be added to dairy products including raw or pasteurised whole milk, skim mil, or modified milk products including flavoured milks, and the resulting mixture processed as described above.

Applicant has found that the total microbial count in liquid colostrum treated according to the process of the present invention is reduced by at least approximately 80%, preferably at least approximately 90%, more preferably at least approximately 95%. For example, a combination of gentle heat treatment at 55° C. and bactofugation typically renders a minimum 99% reduction in total microbial count. Moreover, a substantial proportion of the antibodies and/or growth factors in the liquid colostrum produced according to the method of the present invention remain undenatured following the treatment.

Because of the high concentration of immunoglobulin in the fresh, processed colostrum, only a relatively small proportion of colostrum is required to be added to milk or dairy products to bring the resulting product up to the level of antibodies normally found in pre-processed milk, eg., approximately 10% colostrum processed according to the invention will typically provide 100% as much immunoglobulin or more as pre-processed milk.

Due to the economy and effectiveness of this approach it is now possible to safely provide dairy produce which contains undenatured antibodies and growth factors. The undenatured immunoglobulins may be targeted against specific human diseases or metabolic disorders by hyperimmunising the mammal, providing a very effective palatable form of therapy.

Accordingly, in a second aspect of the present invention there is provided a method of preparing a dairy composition including undenatured antibodies and/or growth factors which method includes adding to a dairy product a liquid colostrum product.

Preferably the liquid colostrum product is from a bovine, ovine or caprine source. Preferably the liquid colostrum product is produced by the process of the present invention. The liquid colostrum product may be added to the dairy product at any time. Preferably, the addition occurs after the dairy product has been pasteurised.

The dairy product may be of any suitable type and includes pasteurised and unpasteurised dairy products such as milk, for example raw or pasteurised full-cream, skim, modified, flavoured milk; yoghurt, for example natural, flavoured, frozen or drinking yoghurt; tonics and sports drinks; and other dairy products such as custards, cheese and cottage cheese formulations, and ice creams.

Preferably the colostrum is added in an amount of approximately 1% w/w to approximately 50% w/w, more preferably approximately 2% w/w to approximately 20% w/w, most preferably approximately 5% w/w to approximately 10% w/w.

In this manner it is possible to provide a milk or other dairy product containing a measurable quantity of undenatured antibodies, preferably at a concentration similar to or greater than that found in raw milk prior to a normal pasteurisation process (eg. approximately 0.2% IgG). Alternatively or in addition the milk or other dairy product may contain undenatured growth factors.

In a still further aspect of the present invention there is provided a dairy composition for human consumption including liquid colostrum that has not been subjected to a drying process.

Preferably, the liquid colostrum product is from a bovine, ovine or caprine source. Preferably the liquid colostrum product is produced by the process of the present invention.

The dairy product may be of any suitable type and includes pasteurised and unpasteurised dairy products such as milk, for example raw or pasteurised full-cream, skim, modified, flavoured milk; yoghurt, for example natural, flavoured, frozen or drinking yoghurt; tonics and sports drinks; and other dairy products such as custards, cheese and cottage cheese formulations, and ice creams.

Preferably, the dairy composition includes approximately 1% w/w to approximately 50% w/w, more preferably approximately 2% w/w to approximately 20% w/w, most preferably approximately 5% w/w to approximately 10% w/w of liquid colostrum.

In this manner it is possible to provide a milk or other dairy product containing a measurable quantity of undenatured antibodies, preferably at a concentration similar to or greater than that found in raw milk prior to a normal pasteurisation process (eg. approximately 0.2% IgG w/w). Alternatively or in addition the milk or other dairy product may contain undenatured growth factors.

The present invention will now be more fully described with reference to the accompanying Examples. It should be understood, however, that the description following is illustrative only and should not be taken in any way as a restriction on the generality of the invention described above.

EXAMPLE 1

Centrifugation of Colostrum

Materials: skimmed colostrum whole colostrum

Apparatus: Alfa Laval D-3187M-60 Bacterial centrifuge

SUMMARY

This study was designed to test the suitability of the Alfa Laval D3187M-60 at reducing bacterial loads in colostrum. The equipment was installed in-line (between Past I and UFS-2) to reduce total bacterial counts with the aim of reliably producing a product with less than 1000 organisms/gram.

PURPOSE

To evaluate the suitability of the Alfa Laval D3187M-60 at reducing total bacterial load in colostrum.

PROCEDURE

Bactofuge D3187M-60 was installed and commissioned on H$_2$O. Flow rates were set at:

inlet=672 Iph outlet=600 Iph bactofugate=72 Iph i) Skimmed colostrum

Skim colostrum was heated to 55° C. for 30 minutes (not pasteurised) and passed through the bactofuge using the parameters outlined above. N.B. heating to 55° C. reduced bacterial count from $2.65 \times 10^7$ to $4.9 \times 10^6$ or 81.5% reduction, which is not suitable for human consumption.

ii) Whole colostrum batch 2B02

Whole colostrum was processed as a complete batch and various microbiological samples taken.

iii) Whole colostrum batch 2B03

Whole colostrum was processed as a complete batch through to powdered stage.

RESULTS i) Skimmed Colostrum

| | |
|---|---|
| Raw colostrum | $2.65 \times 10^7$ cfu/mL |
| Heat treated skim (55° C., 3 min) | $4.9 \times 10^6$ (81.5% reduction) |
| Centrifuged skim | $1.86 \times 10^3$ (99.96% reduction) |
| Total reduction | 99.99% | ii) BATCH 2B02

| | |
|---|---|
| Raw colostrum | $1.22 \times 10^4$ cfu/mL |
| Heat treated (60° C., 30 min) | $6.65 \times 10^2$ (94.5% reduction) |
| Centrifuged skim | 16 (97.6% reduction) |
| Total reduction | 99.9% | iii) BATCH 2B03

| | |
|---|---|
| Raw colostrum | $1.42 \times 10^5$ cfu/mL |
| Heat treated (63° C., 30 min) | $3.2 \times 10^2$ (99.8% reduction) |
| Centrifuged skim | 33 (89.7% reduction) |
| Total reduction | 99.98% |

DISCUSSION

The results indicate that the Alfa Laval DM-3187M-60 Bacterial Centrifuge is effective at removing up to approximately 99% of heat resistant organisms (ie. those organisms surviving heat treatment), providing a total reduction in bioburden from raw colostrum of at least 99.9%.

With a good quality colostrum it is possible to produce good quality concentrate (<100 cfu/mL).

CONCLUSIONS

The Alfa Laval D-3187M-60 Bacterial Centrifuge is effective at removing organisms from colostrum to an extent that it is acceptable for inclusion in dairy products such as milk.

EXAMPLE 2

Reduction of Colony Forming Units After Bacterial Centrifugation

Samples of colostrum were collected. The colostrum was sampled and then treated by firstly separating the colostrum into a light phase (cream) and a heavy phase (skim) before bacterial centrifugation. Samples of each batch (treated and raw) were removed at various stages, including before and after separation into light (cream) and heavy (skim) phases, and before and after bacterial centrifugation. Bacterial counts measured as colony forming units (CFU)/mL were assessed to determine overall reduction of CFU's.

PROCEDURE

Bactofuge D3187M-60 was installed and commissioned on H$_2$O. Flow rates were set at approximately:

inlet=1600 Iph outlet=1440 Iph bactofugate=160 Iph i) Skimmed colostrum

Skim colostrum was heated to 55° C. for 3 minutes (not pasteurised) and passed through the bactofuge using the parameters outlined above.

RESULT

Thirty seven samples of colostrum were processed as outlined above. After bacterial centrifugation the average CFU/ml was 44.97 CFU/ml which represented a 99.86% overall reduction of CFU's from raw colostrum to the processed colostrum product.

CONCLUSION

Clearly the combination of skimmed colostrum heated to 55° C. and centrifuged at the 1600 Lph flowthrough rate is an effective means of reducing bacterial load whilst reducing the incidence of denaturing the biologically active proteins by exposure to high temperatures.

EXAMPLE 3

Dairy Composition

PROCEDURE

The colostrum was processed as described in Example 2. Two separate experiments were conducted. The first was from batch 6F01 which was a batch of low liter colostrum of all failed materials, such that its original bacteriology was very dirty prior to bactofugation. The second was from batch 6F03 which was high titre colostrum of all "A" grade materials such that its original bacteriology was very clean.

The figures for the raw and bacterial centrifuged samples are given in Table 1 below.

TABLE 1

| Sample | Total Count | Coliform | Staphylococcus |
|---|---|---|---|
| 6F01 Raw | 500,00 | 670 | 380,000 |
| 6F01 Bactofuged | 11 | 0 | 0 |
| 6F03 Raw | 1,400 | 4 | 10 |
| 6F03 Bactofuged | 5 | 0 | 0 |

RESULTS

The results for the bacterial centrifuged colostrum from batch 6F01 when added to whole milk and skim milk at 10% are given in Table 2 and compared with milk and colostrum controls:

TABLE 2

| Sample Time | Neat Colostrum | 10% Col./ Whole Milk | 10% Col./ Skim Milk | Whole Milk Control | Skim Milk Control |
|---|---|---|---|---|---|
| Time 0 | 11 | 1,100 | 1,300 | 1,400 | 1,400 |
| 2 days | 15 | 1,200 | 1,200 | 1,100 | 1,400 |
| 4 days | 16 | 1,200 | 1,500 | 1,300 | 1,600 |
| 6 days | 13 | 1,500 | 1,400 | 1,400 | 1,400 |
| 8 days | 12 | 1,200 | 1,400 | 1,200 | 1,600 |
| 10 days | 18 | 1,100 | 1,300 | 1,200 | 1,400 |
| 12 days | 7 | 1,000 | 1,200 | 1,200 | 1,600 |
| 14 days | 9 | 1,000 | 1,600 | 1,100 | 1,100 |

All samples in experiment 1 showed no changes to bacterial load over the test period. Furthermore the neat colostrum and the 10% colostrum in full cream milk sample (samples 1 and 2) continued to be tested. Sample 2 took 30 days to reach 58,000 cfu/mL and sample 1 showed no growth at the 46 day mark.

The results for the bacterial centrifuge bactofuged colostrum from batch 6F03 when added to whole milk and skim milk at 10% are given in Table 3 and compared with milk and colostrum controls.

TABLE 3

| Sample Time | Neat Colostrum | 10% Col./ Whole Milk | 10% Col./ Skim Milk | Whole Milk Control | Skim Milk Control |
|---|---|---|---|---|---|
| Time 0 | 5 | 1,600 | 1,500 | 1,700 | 1,700 |
| 2 days | 7 | 1,400 | 1,500 | 1,500 | 1,400 |
| 4 days | 9 | 1,100 | 1,500 | 1,400 | 1,600 |
| 6 days | 9 | 1,400 | 1,300 | 1,500 | 1,500 |
| 8 days | 4 | 1,200 | 1,200 | 1,500 | 1,600 |
| 10 days | 13 | 7,700 | 6,200 | 5,100 | 15,300 |
| 12 days | 500 | 180,000 | 140,000 | 200,000 | 400,000 |
| 14 days | 74,000 | 32,000,000 | 27,000,000 | 45,000,000 | 61,000,000 |

Samples in experiment 2 showed no difference in bacterial loading between dairy compositions with colostrum processed and those without.

Considering both experiments together it can be seen that the addition of colostrum to full cream or skimmed milk has no affect on the shelf life of those products.

EXAMPLE 4

Stability of Antibodies in Dairy Compositions

AIM

The aim of the study was to assess the stability of colostral antibodies at 4° C. for 14 days.

MATERIAL AND METHODS

Two batches of colostrum 6F01 and 6F03, including high and low titre of antibodies was used for this study. From each batch 10% of colostrum was mixed with whole milk as well as with skim milk. Samples were withdrawn on day 0, 2, 4, 6, 8, 10, 12, 14 from 4° C. and frozen −20° C. until assayed.

The experiment was performed using standard SOP10.01 and each sample was tested three times.

RESULTS

The two tables below showing the result of rotavirus antibodies titre over 14 days, in two batches of colostrum.

TABLE 4

BATCH 6 F03

| Day | Neat Colostrum | 10% Colostrum in Whole Milk | 10% Colostrum in Skim Milk |
|---|---|---|---|
| 0 | 48960 | 4841 | 4874 |
| 2 | 56378 | 4544 | 3963 |
| 4 | 50937 | 4841 | 4348 |
| 6 | 56898 | 5008 | 5415 |
| 8 | 61612 | 5063 | 5750 |
| 10 | 61612 | 5154 | 4829 |
| 12 | 55024 | 3927 | 5803 |
| 14 | 66839 | 5063 | 5334 |

TABLE 5

BATCH 6 F01

| Day | Neat Colostrum | 10% Colostrum in Whole Milk | 10% Colostrum in Skim Milk |
|---|---|---|---|
| 0 | 3263 | 491 | 472 |
| 2 | 2979 | 468 | 458 |
| 4 | 2737 | 468 | 485 |
| 6 | 3062 | 493 | 430 |
| 8 | 2840 | 464 | 462 |
| 10 | 3255 | 549 | 463 |
| 12 | 3115 | 463 | 459 |
| 14 | 3179 | 541 | 465 |

DISCUSSION

Table 6 shows the summary of the results from this study.

TABLE 6

Results of testing rotavirus antibodies in high and low titre milk samples by ELISA.

| | SAMPLE | MEAN | SDEV | COVAR | T-TEST |
|---|---|---|---|---|---|
| POSITIVE | 1 | 57282 | 5908 | 10% | 0.26 |
| BATCH | 2 | 4805 | 403 | 8% | 0.99 |
| 6F03 | 3 | 5040 | 657 | 10% | 0.33 |
| NEGATIVE | 1 | 3054 | 191 | 6% | 0.72 |
| BATCH | 2 | 492 | 37 | 7% | 0.57 |
| 6F01 | 3 | 462 | 16 | 10% | 0.96 |

SAMPLE 1 = neat
SAMPLE 2 = 10% colostrum in whole milk
SAMPLE 3 = 10% colostrum in skim milk

DISCUSSION

The results of this study indicate that rotavirus antibodies measured by ELISA in colostrum are considerably stable at 4° C. over 14 days in the dairy composition according to the invention.

CONCLUSION

This study shows that colostrum prepared according to the invention has very stable rotavirus antibodies and can be stored in the fridge for period of at least 2 weeks with no detrimental effects to the rotavirus antibody titre.

EXAMPLE 5

Taste Testing

PURPOSE

To determine on a small scale if subjects could detect a difference in taste and preference for milk preparations containing various concentrations of freshly processed liquid colostrum.

MATERIALS

Homogenised, full cream milk

Skimmer milk

Iced Coffee milk

Batch 5F01 colostrum obtained directly after separation and bactofugation.

Numbered cups.

METHODS

Three experiments were carried out to determine the effect colostrum had on the taste of 3 types of milk.

Experiment One

Colostrum was mixed with Iced coffee milk product in the proportions: 0%, 2%, 8%, 20%. The different products were put into numbered cups, and subjects asked to taste each product and rank the numbered cups in order of taste preference.

| Concentration % | Cup No. |
| --- | --- |
| 0 | 3 |
| 2 | 1 |
| 8 | 2 |
| 20 | 4 |

RESULTS:

| Person | Ranking | | | | Comments |
| --- | --- | --- | --- | --- | --- |
| AS | 3 | 4 | 2 | 1 | 2 creamiest, 1 more like skim |
| GP | 3 | 4 | 2 | 1 | 3 is the iced coffee product, 4 is most like real coffee |
| RP | 1 | 4 | 2= | 3= | did not like 2 or 3 |
| RR | = | = | = | = | no difference |
| CC | = | = | = | = | all nice |
| JP | = | = | = | = | all OK |

The results from experiment one indicate that:
1. Subjects were not able to detect taste difference to ice coffee milk when separated bactofuged colostrum from batch 5F01 was added up to 20% w/w.
2. Cups 3 and 4 were preferred by two subjects. These products respectively contained 0% and 20% colostrum, again indicating that the addition of colostrum does not significantly affect taste preference.

Experiment Two

Colostrum was mixed with homogenised full cream milk product in the proportions: 0%, 2%, 8%, 20%. The different products were put into numbered cups, and subjects asked to taste each product and rank the numbered cups in order of taste preference.

| Concentration % | Cup No. |
| --- | --- |
| 0 | 2 |
| 2 | 4 |
| 8 | 1 |
| 20 | 3 |

RESULTS:

| Person | Ranking | | | | Comments |
| --- | --- | --- | --- | --- | --- |
| AS | 3 | 2 | = | = | On first tasting, 3 seemed best. On second tasting, 2 seemed best |
| PW | 3 | 1 | 2 | 4 | Not really much difference |
| RP | = | = | = | = | Couldn't tell, all tasted bad. |
| BC | 2 | 1 | 4 | 3 | |
| MS | 2 | 3 | 4 | 1 | All Ok, can't tell much difference |
| JT | 1= | 4= | 3= | 2 | Only 2 seemed worse |

The results from experiment two indicate that:
1. Subjects were not able to detect taste difference to milk when separated bactofuged colostrum from batch 5FO1 was added up to 20% w/w.
2. Cups 2 and 3 were preferred by two subjects each. These products respectively contained 0% and 20% colostrum, again indicating that the addition of colostrum does not significantly affect taste preference.
3. One person ranked the 20% colostrum worst, while one ranked the 0% colostrum worst. The person ranking the 20% colostrum worst ranked the normal product best. This was the only person to get close to ranking taste preferences according to colostrum content.

Experiment Three

Colostrum was mixed with skimmer milk product in the proportions: 0%, 4%, 16%, 40%. The different products were put into numbered cups, and subjects asked to taste each product and rank the numbered cups in order of taste preference.

| Concentration % | Cup No. |
| --- | --- |
| 0 | 1 |
| 4 | 2 |
| 16 | 3 |
| 40 | 4 |

RESULTS:

| Person | Ranking | | | | Comments |
| --- | --- | --- | --- | --- | --- |
| AS | 1 | 2 | 3 | 4 | Colour difference was noticeable, taste OK. |
| PW | = | = | = | 3 | 3 was least liked |
| RP | 2 | 3 | 1 | 4 | |
| BC | 1 | 3 | 2 | 4 | |
| MSp | 2 | 3 | 4 | 1 | All OK, can't tell which is milk, 4 is richer; 2 is creamier than 1. |
| MS | 1 | 2 | 4 | 3 | |

The results from experiment three indicate that:
1. When colostrum from batch 5F01 was added to skimmer milk, at the higher concentrations, a difference was noticeable, both in colour and mouth feel.
2. Cup 4 (40% colostrum) was ranked bottom, taste was acceptable, just noticeably different.

CONCLUSION

Overall the study indicates that fresh, skim, bactofuged colostrum similar to that produced in batch 5F01 should be an acceptable additive to white milk and flavoured milk in the proportion intended (approximately 20% or less). Only when added to skim at 16% or more is there likely to be a noticeable difference.

Finally, it is to be understood that various alterations, modifications and/or additions may be made without departing from the spirit of the present invention as outlined herein.

What is claimed is:

1. A method of preparing a dairy composition comprising undenatured antibodies, growth factors or a mixture thereof which method includes adding to a dairy product a liquid colostrum product prepared by a process which comprises the steps of subjecting colostrum to flow-through centrifugation to substantially reduce the microbial content thereof, wherein the centrifugation is performed by controlling throughput and thereby residence time of the colostrum during centrifugation.

2. A method according to claim 1 wherein the liquid colostrum product is added after pasteurisation of the dairy product.

3. A method according to claim 1 wherein the liquid colostrum product is added in an amount of approximately 1% w/w to approximately 50% w/w.

4. A method according to claim 1 wherein the colostrum is added in an amount of approximately 2% w/w to approximately 20% w/w.

5. A method according to claim 1 wherein the colostrum is added in an amount of approximately 5% w/w to approximately 10% w/w.

6. A dairy composition prepared by the method according to claim 1.

7. A dairy composition according to claim 6 including a measurable quantity of undenatured antibodies and/or growth factors at a concentration similar to or greater than that found in raw dairy products prior to normal pasteurisation processes.

8. A dairy composition according to claim 1 including a dairy product selected from the group including pasteurised and unpasteurised dairy products including milk which is raw or pasteurised, full-cream, skim, modified or flavoured milk; yoghurt, including traditional natural, flavoured, frozen or drinking yoghurt; tonics and sports drinks; and other dairy products including custards, cheese and cottage cheese formulations, and ice creams.

* * * * *